United States Patent [19]
Bruder et al.

[11] Patent Number: 5,634,469
[45] Date of Patent: Jun. 3, 1997

[54] METHOD FOR LOCALIZING A SITE OF ORIGIN OF AN ELECTRICAL HEART ACTIVITY

[75] Inventors: Herbert Bruder, Hoechstadt; Reinmar Killmann, Forchheim, both of Germany

[73] Assignee: Siemens Aktiengesellschaft, Munich, Germany

[21] Appl. No.: 622,688

[22] Filed: Mar. 26, 1996

[30] Foreign Application Priority Data

Mar. 29, 1995 [DE] Germany .................. 195 11 532.5

[51] Int. Cl.$^6$ .................................................. A61B 5/0462
[52] U.S. Cl. ............................................................ 128/699
[58] Field of Search ............................. 128/696, 699

[56] References Cited

U.S. PATENT DOCUMENTS 5,311,867  5/1994  Kynor .

FOREIGN PATENT DOCUMENTS 3732122  4/1989  Germany .
4307545  9/1994  Germany .

OTHER PUBLICATIONS

"Solving the Inverse Problem in Magnetocardiography," IEEE Trans. Eng. Med. Biol., Aug./Sep. 1994, pp. 487–496.
"Boundary Element Solution of Biomagnetic Problems," Bömmel et al., IEEE Trans. Mag., vol. 29, No. 2 Mar. 1993, pp. 1395–1398.
"Localization of the Site of Origin of Postinfarction Ventricular Tachycardia by Endocardial Pace Mapping," SippensGroenewegen et al., Circulation, vol. 88, No. 5, Part 1, Nov. 1993, pp. 2290–2306.
"Body Surface Mapping of Ectopic Left and Right Ventricular Activation," SippensGroenewegen et al., Circulation, vol. 82, No. 3, Sep. 1990, pp. 879–896.
"Three–Dimensional Computer Model of the Entire Human Heart for Simulation of Reentry and Tachycardia: Gap Phenomenon and Wolff–Parkinson–White Syndrome," Killmann et al., Basic Research in Cardiology, vol. 86, 1991, pp. 485–501.
"Principal Component Analysis," Wold et al., Chemometrics and Intelligent Laboratory Systems, vol. 2, 1987, pp. 37–52.
"The Use of Temporal Information in the Regularization of the Inverse Problem of Electrocardiography," Oster et al., IEEE Trans. Biomed. Eng., vol. 39, No. 1, Jan. 1992, pp. 65–75.

*Primary Examiner*—William E. Kamm
*Assistant Examiner*—Scott M. Getzow
*Attorney, Agent, or Firm*—Hill, Steadman & Simpson

[57] ABSTRACT

In a method for localizing an origination site of electrical heart activity, body surface potentials generated by the heart activity are measured at a number of measuring points with a multi-channel measuring system, and values are stored that characterize the body surface potentials at the measuring points. These values are then compared to comparison values stored in a data bank, the comparison values representing comparison surface potentials that arise from modeled comparison heart activities whose position in the heart is known. The position of that comparison heart activity whose comparison values exhibit the most similarity to the characteristic values is emitted as a localization result. The comparison values are determined using a heart model embedded in a thorax model.

6 Claims, 2 Drawing Sheets

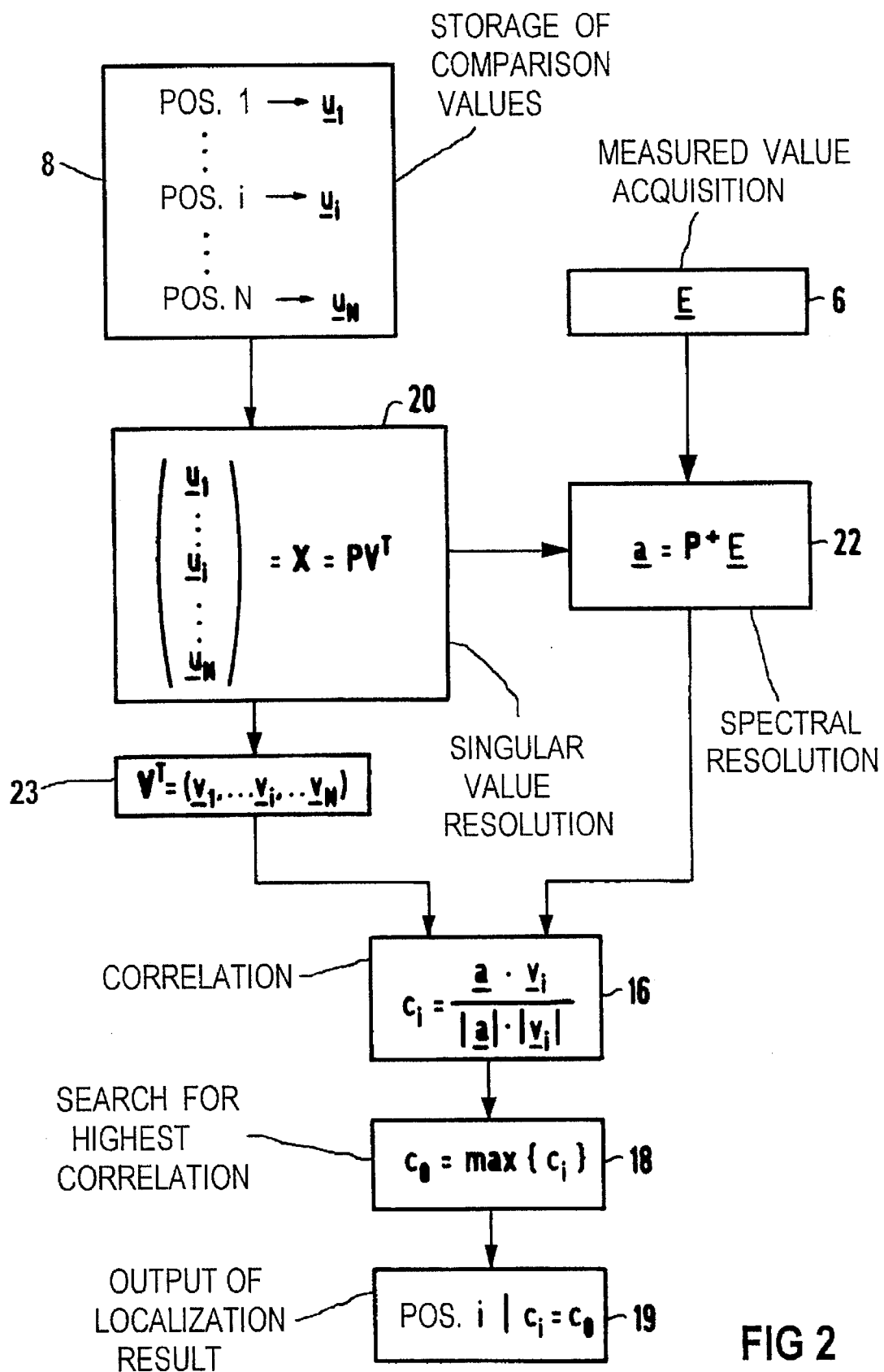

METHOD FOR LOCALIZING A SITE OF ORIGIN OF AN ELECTRICAL HEART ACTIVITY

BACKGROUND OF THE INVENTION

1. Field of the Invention

The invention is directed to a method for localizing (identifying) a site of origin of an electrical heart activity. More specifically the invention is directed to such a localization method of the type wherein body surface potentials generated by the heart activity are measured at a number of measuring points with a multi-channel measuring system and values that characterize the body surface potentials at the measuring points are stored. These values are compared to comparison values stored in a databank, the comparison values characterize comparison surface potentials that arise from comparison heart activities whose position in the heart is known, and the position of that comparison heart activity whose comparison values exhibit the most similarity to the characteristic values is emitted as the site of origin of the heart activity in question.

2. Description of the Prior Art

A method of the type generally described above is known from an article by Sippens-Groenewegen et al. entitled, "Localization of the Site of Origin of Postinfarction Ventricular Tachycardia by Endocardial Pace Mapping", Circulation, Volume 88, No. 5, Part 1, November 1993, pp. 2290–2306. Body surface potentials of electrical heart activities are simultaneously taken at the thorax surface with sixty-two electrodes. These signals are integrated over the QRS complex. The integrated measured value, as a characteristic value, is then compared to corresponding comparison values that arise from comparison heart activities originating from a known position. The position of that comparison heart activity whose comparison values agree best with the characteristic values is emitted as the localization result.

Details of how the comparison values of comparison heart activities are generated are set forth in the article by Sippens-Groenewegen et al. entitled, "Body Surface Mapping of Ectopic Left and Right Ventricular Activation, Circulation, Volume 82, No. 3, September 1990, pp. 879–896. According thereto, comparison surface potentials are measured for healthy persons with a multiple electrode arrangement, these comparison surface potentials being generated by a stimulation catheter in the heart. The location of the catheter is determined by means of a biplanar (stereo) cineradiographic method. The compilation of sufficiently large number of comparison heart activities and the associated comparison body surface potentials for the localization is extremely complicated because of the required measurements of both healthy patients and patients exhibiting pathological cardiac activity.

An article by Killmann et al. entitled "Three-dimensional computer model of the entire human heart for simulation of reentry and tachycardia: gap phenomenon and Wolff-Parkinson-White syndrome", Basic Research in Cardiology, Volume 86, 1991, pp. 485–501, discloses a computer model for the simulation of normal and pathological ECG data. In the heart model, the heart is divided into volume cells that are interconnected according to the heart physiology. Electrophysiological parameters are allocated to each cell. In particular, the parameters of conduction velocity refractory period and cycle length are allocated to the cells. These can be freely selected within the scope of physiologically meaningful values. Proceeding from a stimulation at the sinus node, the individual volume cells are subsequently activated in the modelled stimulation propagation in accord with the electrophysiological parameters allocated to them. The stimulation propagation is accompanied by an electrical field from which body surface potentials can be calculated. The cells have a size of about 2.5 mm.

A method for calculating comparison surface potentials is disclosed in the article by Bömmel et al., "Boundary Element Solution of Biomagnetic Problems", IEEE Trans. Magn. MAG-29, 1993, pp. 1395–1398. With the assistance of a modified boundary element method, electrical values generated by a heart model am utilized for the calculation of the distribution of body surface potentials on a thorax model.

A method of principal component analysis as disclosed, for example, in the article by Wold et al., "Principal Component Analysis", Chemometrics and Intelligent Laboratory Systems, Volume 2, 1987, pp. 37–52, is known for use in reducing large datasets to their characteristic informational content.

German OS 43 07 545 discloses an apparatus and a method for identifying the location and/or extent of ischemia and/or infarctions in the heart of a subject. Measured ECG values are supplied to a neural network therein. With the assistance of the aforementioned heart model, a neural network is correspondingly trained to emit the location and/or the extent of pathological modifications from the ECG data. The preparatory outlay for realizing a neural network that is suitable for resolving the localization task, however, is high.

SUMMARY OF THE INVENTION

An object of the present invention is to provide a method for localizing an electrical heart activity with which an adequately exact and fast localization can be implemented.

This object is achieved in a method in accordance with the principles of the present invention wherein the comparison values are determined using a heart model embedded in a thorax model. Without having to examine a large number of patients, comparison heart activities can be arranged in an adequately tight spatial grid and the comparison values belonging thereto can be determined. The comparison values can then be stored in a structure similar to a data bank.

In one embodiment, normalized correlation coefficients are formed for the comparison from the characteristic values with the comparison values of every comparison heart activity, the position of the comparison heart activity whose comparison values have the highest correlation coefficient with the characteristic values being emitted as the localization result. The normalized correlation coefficient of the functions to be compared is a similarity criterion adequate for achieving the localization task. In particular, amplitude differences have no influence on the similarity criterion given an otherwise identical signal curve.

In a further embodiment, the comparison is limited to the QRS complex in the body surface potentials. Pathological electrical heart activities primarily influence the course of the body surface potentials in the ORS complex.

In another embodiment, the characteristic values reproduce the time curve of the body surface potentials at the measuring points. Although a large number of characteristic values must be correlated for this purpose with a corresponding number of comparison values, it has been found that the time curve of the comparison surface potentials reacts less sensitively to variations in the geometry of the thorax model. Departures of the patient's anatomy from the selected thorax model therefore have only a slight influence on the precision of the localization result.

In a further embodiment, components of a measured value vector are formed from discrete values of the time curve of the body surface potentials at the measuring points, with a corresponding comparison vector existing for each position of the comparison heart activity. The measured value vector is compared to each comparison vector by forming a scalar product of the two vectors, with each of the two vectors being normalized with respect to its magnitude, and the position (origin) of the comparison heart activity whose comparison vector forms the largest normalized scalar product with the measured value vector is emitted as the localization result.

According to another embodiment, a data reduction can be achieved by extracting eigenvectors from the discrete-value time curve of comparison surface potentials arising from comparison heart activities, representing the characteristic values as measured expansion coefficients resulting from a spectral decomposition of the discrete-value time curve of the body surface potentials measured at the measuring points defined by the eigenvectors, and obtaining, as a comparison result, comparison expansion coefficients that are the result of a spectral resolution of the discrete-value time curve of the comparison surface potentials.

DESCRIPTION OF THE DRAWINGS

FIG. 2 is a block diagram illustrating a second version of the localization method of the invention wherein a correlation of expusion coefficients that represent the result of a spectral decomposition according to eigenvectors is implemented.

DESCRIPTION OF THE PREFERRED EMBODIMENTS

Figure 1:
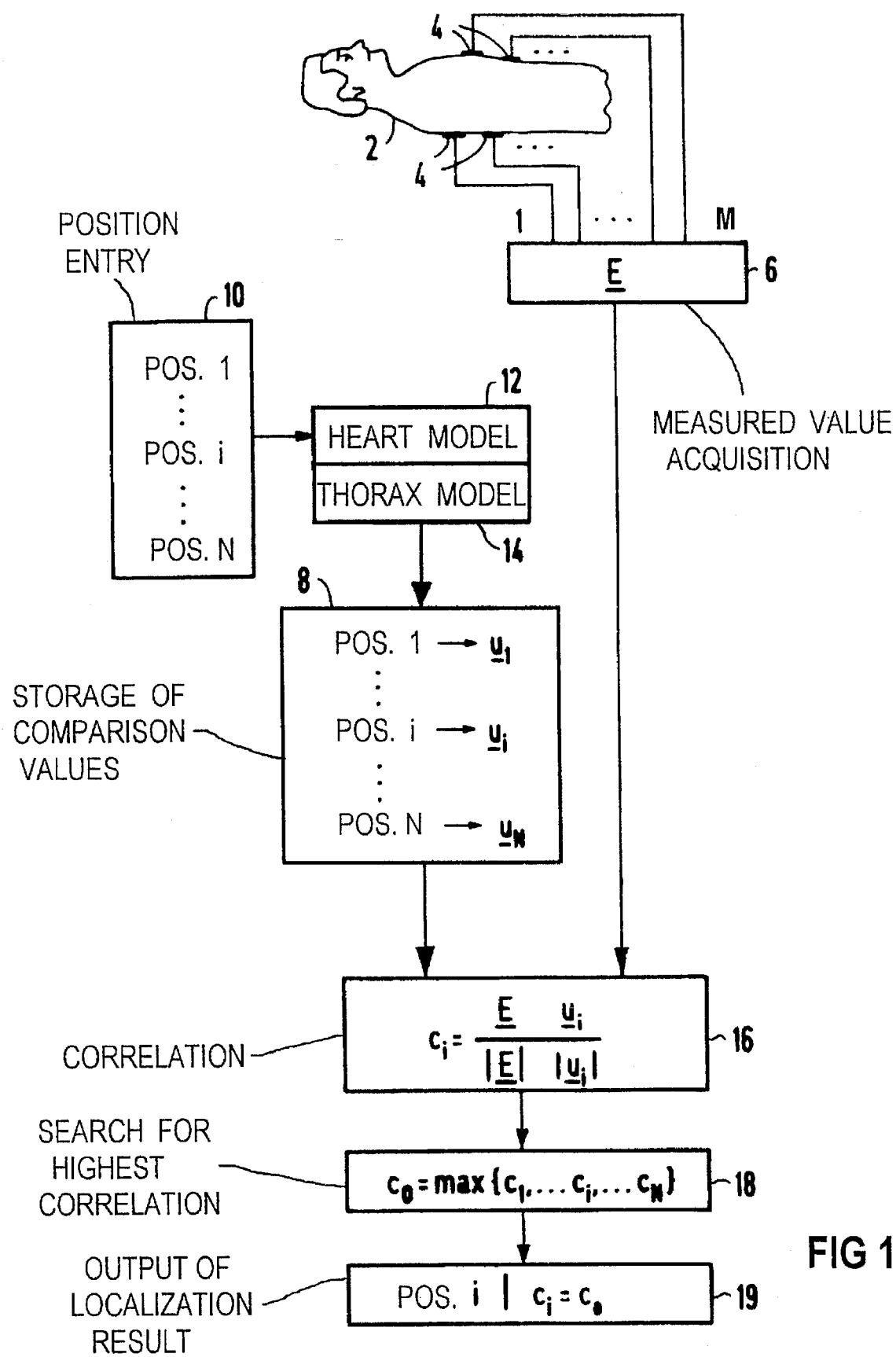
FIG 1 is a block diagram illustrating a first version of the localization method of the invention, wherein a spatial-chronological correlation is implemented.

In a schematic illustration of the first version of the inventive localization method, FIG I shows a torso of a patient 2 on whom body surface potentials generated by heart activities are measured at, for example, sixty-four positions, anterior and posterior, with electrodes 4. The QRS complex from the measured signal curves is interpreted here since many pathologies are expressed in abnormal QRS signals. The measured values of each electrode 4 (or of each measurement channel) are sampled, with approximately $K=50-60$ QRS signal values typically being generated given a sampling frequency of 500 Hz. These values are considered as components of a measured value vector $\underline{E}$. Accordingly, the measured value vector $\underline{E}$ has $L=M \times K=64 \times 50$ components that are entitled or stored in the acquisition step 6 in, for example, the time sequence with which the signal is sampled. For example, the first component of the measured value vector $\underline{E}$ corresponds to the value of the potential of measurement channel 1 at the first sampling time, the second component corresponds to the measured value of the potential of the measurement channel 2 at the first sampling time, etc.

Comparison values $\underline{u}_i$ are stored in a data bank 8. Analogously to the measured body surface potentials, the comparison values $\underline{u}_i$ reproduce comparison surface potentials of comparison heart activities whose position (origination site) 10 in the heart is known. The data bank contains $i=1$ through $i=N=244$ comparison surface potentials, corresponding to a grid spacing in the heart model of approximately 0.75 cm through 1 cm of the comparison heart activities. The comparison heart activities together with the associated comparison surface potentials are generated by means of a heart model 12, as disclosed in the initially cited article by Killmann et al. The heart model 12 that allows the comparison surface potentials to be calculated is embedded in a thorax model 14.

A suitable thorax model is known from the initially cited article by Bömmel et al. The advantage of determining the comparison surface potentials from the heart model 12 embedded in the thorax model 14 is that the locations of the comparison heart activities can be varied and the associated comparison surface potentials can be calculated in a nearly arbitrary density. In particular, the density of the locations of the comparison heart activities can be defined according to physiological considerations. Care must be exercised in the calculation of the comparison surface potentials to insure that the arrangement of the points at which the comparison surface potentials are calculated coincides with the actual arrangement of the electrodes 4 of the multi-channel measuring arrangement.

In a correlation step 16, a normalized correlation coefficient $c_i$ is formed for each position $i=1$ through $i=N$, this representing the scalar product of the comparison values of potential $\underline{u}_i/|\underline{u}_i|$ normalized with respect to magnitude with the measured value vector $\underline{E}/|\underline{E}|$, also normalized with respect to magnitude. When all normalized correlation coefficients $c_i$ are present, the highest correlation coefficient $c_o$ is sought in a search step 18. The position of the comparison heart activity belonging to the correlation coefficient $c_o$ constitutes the localization result for the heart activity represented by the measured value vector $\underline{E}$. In an output step 19 the position of the comparison heart activity is emitted that has been found as the localization result.

A data reduction both of the comparison values $\underline{u}_i$ and of the measured values $\underline{E}$ can, as shown in function blocks in FIG. 2, ensue by means of a spectral decomposition of the vectors $\underline{u}_i$ and $\underline{E}$ according to the technique of principal component analysis. A matrix X that contains the comparison surface potentials $\underline{u}_i$ stored in the data bank 8 forms the data base for this analysis. A singular value decomposition 20 is implemented for the matrix X, so that the matrix X is represented as a matrix product $$X = USV^T.$$

The matrix U is an orthogonal $L \times L$ matrix that contains the eigenvectors of $XX^T$. V is an orthogonal $N \times N$ matrix that contains the eigenvectors of $X^TX$, With $V^T=(\underline{V}_1, \ldots \underline{V}_N)$ being obtained in step 23. The matrix S is the $L \times N$ matrix of the singular values.

A matrix $P=US$ is defined, so that $$X = PV^T$$

is valid.

The $L \times N$ matrix $P=(\underline{P}_1, \ldots \underline{P}_N)$ contains the N eigenvectors of the signal space of $XX^T$, what are referred to as the principal components. The spectral decomposition of a signal vector $\underline{u}_i$ consequently is $$\underline{u}_i = \sum_{l=1}^{N} V_{il} \times \underline{P}_l, (1 \leq i \leq N).$$

The measured value vector $\underline{E}$ is correspondingly subjected to a spectral resolution. in step 22. To that end, the generalized inverse or Moore Penrose inverse $P^+$ of the matrix P of the N eigenvectors of the signal space of $XX^T$ must be formed. The expansion coefficients $\underline{a}$ associated with the signal $\underline{E}$ are then correspondingly formed in a matrix multiplication step 24:

$$\underline{a} = P^+\underline{E}.$$

The comparison in a correlation step 16 ensues corresponding to that already described on the basis of FIG 1 in that scalar products $c_1$ are formed from the normalized expansion coefficients $\underline{a}/|\underline{a}|$ of the measured value vector $\underline{E}$ and the normalized comparison expansion coefficients $\underline{V}/|\underline{V}_i|$. Subsequently, the highest correlation coefficient $C_o$ is sought. The position of the comparison heart activity belonging thereto is then emitted as the localization result.

As noted above, the measured value acquisition can be undertaken using an ECG apparatus, or some other suitable type of extracorporeal cardiac signal-gathering apparatus. The various calculating and storing steps can be undertaken in a computer or processor having sufficient memory capacity, and the emission of the localization result can take place in an output unit, which may include a visual display.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for localizing an origination site of electrical heart activity comprising the steps of:

providing a heart model and providing a thorax model and embedding said heart model in said thorax model, and storing said comparison values in a data bank;

using said heart model embedded in said thorax model, generating a plurality of comparison values representing modeled heart activities respectively originating at a plurality of known positions;

measuring body surface potentials produced by heart activity of a subject at a plurality of measuring points using a multi-channel measuring system and obtaining measured values respectively representing the body surface potentials at said measuring points, generating a characteristic value from said measured values and storing said characteristic value;

comparing said characteristic value to each of said comparison values in said data bank and identifying a comparison value having a highest similarity to said characteristic value; and identifying the known position of said comparison value having the highest similarity to said characteristic value and emitting said position as the site of origin of the heart activity which produced said body surface potentials.

2. A method as claimed in claim 1 wherein the step of comparing said comparison values and said characteristic value comprises:

forming a first set of normalized correlation coefficients from each of said comparison values and forming a second set of normalized correlation coefficients from said measured values as said characteristic value;

correlating each of said first sets with said second set of correlation coefficients to identify correlation coefficients in a first set having a highest correlation with correlation coefficients in said second set; and using said correlation coefficients in said first set having the highest correlation with correlation coefficients in the second set as said comparison values having the highest similarity to said characteristic value.

3. A method as claimed in claim 1 wherein the step of generating said characteristic value from said measured values comprises generating a characteristic value identifying the QRS complex of said subject from said body surface potentials, and wherein the step of generating said comparison values comprises generating comparison values respectively representing a modeled QRS complex from said heart model embedded in said thorax model.

4. A method as claimed in claim 1 wherein the step of generating said characteristic values comprises generating a characteristic value reproducing a chronological curve of said body surface potentials at the respective measuring points.

5. A method as claimed in claim 4, comprising the further steps of:

selecting successive discrete values of said chronological curve of said body surface potentials at the respective measuring points and forming a measured value vector therefrom;

generating a plurality of comparison vectors respectively for each known position of heart activity from said heart model embedded in said thorax model;

comparing said measured value vector to each comparison vector by forming a plurality of scalar products respectively of said measured value vector and each comparison vector;

identifying a highest scalar product of said plurality of scalar products and identifying the position of the heart activity associated with the comparison vector which produced said highest scalar product; and using the position of the activity associated with said comparison vector which produced the highest scalar product as said side of origination of said heart activity which produced said body surface potentials.

6. A method as claimed in claim 1 comprising the further steps of:

generating a chronological curve of modeled comparison surface potentials from heart activity in said heart model embedded in said thorax model and identifying successive discrete values of said chronological curve of modeled comparison surface potentials;

extracting eigenvectors from said discrete values of said time curve of modeled comparison surface potentials;

generating a chronological curve of said body surface potentials measured at the respective measuring points and identifying successive discrete values of said chronological curve of said body surface potentials;

conducting a spectral decomposition of said discrete values of said chronological curve of said body surface potentials to obtain a plurality of measured development coefficients;

conducting a spectral decomposition of said discrete values of said chronological curve of said comparison surface potentials to obtain a plurality of comparison expansion coefficients; and comparing said expansion coefficients associated with the measurement signal and comparison expansion coefficients end identifying comparison expansion coefficients having a greatest similarity to said expansion coefficients associated with the measurement signal and using the known position of the modeled position surface potentials which produced said comparison expansion coefficients having the highest similarity to said expansion coefficient associated with the measurement signal as the site of origin of said heart activity which produced said body surface potentials.

\* \* \* \* \*